(12) United States Patent
Anderson et al.

(10) Patent No.: US 9,453,849 B2
(45) Date of Patent: Sep. 27, 2016

(54) METHODS FOR STAINING CELLS FOR IDENTIFICATION AND SORTING

(75) Inventors: Amy L. Anderson, Prospect Heights, IL (US); Christopher R. Knutson, Chicago, IL (US); Daniel Mueth, Chicago, IL (US); Joseph Plewa, Park Ridge, IL (US); Evan Tanner, Chicago, IL (US)

(73) Assignee: PREMIUM GENETICS (UK) LIMITED, Nantwich (GB)

( * ) Notice: Subject to any disclaimer, the term of this patent is extended or adjusted under 35 U.S.C. 154(b) by 703 days.

(21) Appl. No.: 12/379,063

(22) Filed: Feb. 11, 2009

(65) Prior Publication Data

US 2009/0226880 A1 Sep. 10, 2009

Related U.S. Application Data

(63) Continuation of application No. 11/048,101, filed on Feb. 1, 2005, now abandoned.

(51) Int. Cl.
*G01N 33/50* (2006.01)
*G01N 33/68* (2006.01)
*B82Y 5/00* (2011.01)
*B82Y 10/00* (2011.01)

(52) U.S. Cl.
CPC ............ *G01N 33/689* (2013.01); *B82Y 5/00* (2013.01); *B82Y 10/00* (2013.01); *G01N 33/5005* (2013.01)

(58) Field of Classification Search
CPC .................... G01N 33/689; G01N 33/5005
See application file for complete search history.

(56) References Cited

U.S. PATENT DOCUMENTS

| | | | |
|---|---|---|---|
| 6,416,959 B1 * | 7/2002 | Giuliano et al. | 435/7.2 |
| 2002/0042042 A1 * | 4/2002 | Fahy | 435/1.3 |
| 2002/0115208 A1 * | 8/2002 | Mitchell et al. | 435/325 |
| 2003/0054365 A1 * | 3/2003 | Xu et al. | 435/6 |
| 2004/0217297 A1 * | 11/2004 | Moses et al. | 250/441.11 |
| 2005/0153354 A1 * | 7/2005 | Gilmanshin | 435/6 |

FOREIGN PATENT DOCUMENTS

| | | |
|---|---|---|
| JP | 64-074451 A | 3/1989 |
| JP | H-07-286953 A | 10/1995 |
| JP | 2003-106980 A | 4/2003 |
| JP | 2003-515738 A | 5/2003 |
| WO | WO-01/40766 A1 | 6/2001 |
| WO | WO 02/41906 * 5/2002 | A61K 35/52 |

OTHER PUBLICATIONS

Drobnis et al., "Cold Shock is Due to Lipid Phase Transitions in Cell Membranes: A Demonstration Using Sperm as a Model", The Journal of Experimental Zoology, 1993, vol. 265, No. 4, pp. 432-437.*

Drobnis et al., "Cold Shock is Due to Lipid Phase Transitions in Cell Membranes: A Demonstration Using Sperm as Model", The Journal of Experimental Zoology, 1993, vol. 265 No. 4, pp. 432-437.*

Molecular Probes, "Influx Pinocytic Cell-Loading Reagent (I-14402)", 2001, pp. 1-7.*

Márián et al., Hypo-osmotic shock induces an osmolality-dependent permeabilization and structural changes in the membrane of carp sperm. The Journal of Histochemistry and Cytochemistry, vol. 41., No. 2 (1993) pp. 291-297.*

Parks, John E., Processing and handling bull semen for artificial insemination—don't add insult to injury! Department of Animal Science, Cornell University, (Feb. 1, 2001), [retrieved on May 29, 2015]. Retrieved from the Internet: <URL:http://www.ansci.cornell.edu/pdfs/bullsemen.pdf>.*

* cited by examiner

*Primary Examiner* — Kara Johnson
(74) *Attorney, Agent, or Firm* — McAndrews, Held & Malloy, Ltd.

(57) ABSTRACT

The present invention provides novel methods of cell staining, such as bovine sperm, using electroporation or osmolality treatments at viability-enhancing temperatures. Furthermore, methods of highly efficient cell sorting that are especially suitable in sorting bovine sperm using novel cell staining procedures are also provided.

20 Claims, 2 Drawing Sheets

METHODS FOR STAINING CELLS FOR IDENTIFICATION AND SORTING

CROSS-REFERENCE TO RELATED APPLICATIONS

This application is a continuation application of U.S. patent application Ser. No. 11/048,101, filed Feb. 1, 2005, now abandoned, and incorporates by reference related U.S. patent application Ser. No. 11/046,896, also filed Feb. 1, 2005.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

FIELD OF THE INVENTION

The invention relates to techniques and systems for visualizing live cells using novel staining procedures.

BACKGROUND OF THE INVENTION

The in vivo identification of a target cell population is required, and required quickly, in many industries. Such applications include those where the selected cells are destined for other applications that require the cells to be living after identification. For example, cells are processed using fluorescence-activated cell sorting, where cells are cultured and expanded in vitro after sorting, or in sperm sorting by gender in animal husbandry applications.

Being able to pre-select animal offspring gender would allow more efficient operations of livestock producers. Dairy farmers have little use for most bull calves. For example, males are preferred in beef cattle and sheep because males grow faster, producing more meat more quickly.

The male reproductive cells, the sperm, determine the gender of the offspring. Most males carry an X and a Y sex chromosome, whereas females carry two X chromosomes. A sperm or an egg contains one half of that parent's genetic information; however, the egg only carries an X chromosome one of each pair of autosomes. In mammals, the egg always contains an X chromosome, while the sperm carries either an X or Y chromosome.

Distinguishing male-producing from female-producing sperm is most easily accomplished by exploiting the difference in the size of the two sex chromosomes. The X chromosome contains more DNA than does the Y chromosome. For example, the difference in total DNA between X-bearing sperm and Y-bearing sperm is 3.4% in boar, 3.8% in bull, and 4.2% in ram sperm.

Distinguishing Cells

To illuminate the workings of cells or distinguish cells that differ from each other by the slightest difference (e.g., expression of a particular molecule), various visualization methods have been used for decades, from simple light microscopic observations to high-voltage electronic microscopy. In most of these techniques, cells or tissue are preserved, usually using a cross-linking agent such as an aldehyde (proteins, e.g., glutaraldehyde and formaldehyde), osmium (lipids) or by precipitating parts of the cells, such as cold methanol and proteins. These techniques suffer from the preparation processes that allow for the visualization. Fixation procedures often incur artifacts; for example, in the early days of electronic microscopy (EM), multilamellar bodies were observed but were later understood to be mostly by-products of the fixation protocols, not actual structures found in living mammalian cells. While fixation protocols do preserve some of the cell structure, there are many structures that are difficult to preserve, or when preserved under appropriate conditions, the rest of the cell architecture is destroyed. Classically, this has been the case for the cytoskeleton, especially for exceptionally dynamic microtubules.

To overcome the limitations of visualization techniques in fixed samples, "in vivo" approaches have been explored. For example, to understand where native polypeptides localize, those polypeptides have been purified, associated with a detectable dye (usually covalently), and then introduced into the cell of interest and observed (Chamberlain and Hahn, 2000). This approach does offer the advantages of non-fixed cells; however, the time and expense to purify a target polypeptide, conjugate it to a dye, and then to microinject (a task requiring specialized equipment, experience, skill and patience) the complex into a cell often outweigh the advantages. Furthermore, only limited numbers of cells could be examined at any given time due to the limitations of microinjection.

With the advent of the discovery of green and other visible fluorescent proteins (VFPs), however, the ability to visualize polypeptides—even polypeptide-polypeptide interactions—became facile and less riddled with artifacts. Green fluorescent protein is a naturally occurring luminescent protein first found in jellyfish. Having been cloned, many variants have been produced that produce a rainbow of colors. In most instances, the protein of interest is fused by recombinant procedures to a VFP of choice and the transgene introduced and expressed in the cell of interest (Chamberlain and Hahn, 2000). While this approach is far superior to previous methods, many extra, time-consuming, steps are required from identifying the protein of interest to actually visualizing it in a living cell.

Going beyond cellular localization and movement of proteins, other dyes have been exploited to identify other processes or stain specific molecules. For example, calcium-mediated signaling is monitored in living cells using the fura series of dyes. Other fluorescent dyes have been used to test the molecular size barriers of gap junctions in, for example, epithelial cells. Finally, other stains target specific molecules, such as double-stranded deoxyribonucleic acid (DNA); such stains include some of the Hoechst series of dyes, propidium iodide and ethidium bromide.

In each case, however, the challenge of introducing the dye or stain into a living cells to the appropriate target area is hindered by the cell membrane which provides a barrier to cells from the outside world. In many cases, dyes are membrane impermeant due to their hydrophobic nature or their size; even membrane-permeant dyes can require long incubation times to breach the membrane and reach the target molecules or cellular compartments. Breaching the barrier requires a physical perturbation of the membrane, such as by microinjection or fixation.

Available procedures are few and when available, often face uncompromising challenges. Even traditional methods of staining DNA in common methods of sorting sperm cells by gender require extensive incubation times at elevated temperatures (e.g., 60 minutes at 35° C.; (Johnson, 1992)), permitting quality degradation of the cells. In addition, staining must be sufficient so that the signal can be accurately and precisely detected.

SUMMARY OF THE INVENTION

In a first aspect, the invention discloses methods for staining cells, such as sperm, including bovine sperm, wherein the sperm are mixed with a dye of choice and then electroporating them to facilitate the introduction of the dye. The sperm can be incubated at temperatures that enhance sperm viability, typically equal to or less than 39° C.

In a second aspect, the invention discloses methods for sorting cells, such as sperm, by distinguishing differences in DNA content. The cells are stained with a DNA specific dye by mixing the sperm with the dye and then electroporating them. The sperm can be maintained at temperatures that enhance sperm viability, typically equal to or less than 39° C. The sperm are then passed before an excitation light source causing the stained DNA to fluoresce, and then passed through means for detecting the fluorescence and a means for cell sorting, wherein the cells are sorted by DNA content, and the sorted sperm collected. The methods and apparatus are appropriate for mammalian sperm sorting, such as those from bovine, swine, rabbit, alpaca, horse, dog, cat, ferret, rat, mouse and buffalo. Both membrane permeant and impermeant dyes can be used. Useful dyes include those from the SYTOX blue, orange and green series, cyanine dimers and monomers, POPO-1, BOBO-1, YOYO-1, TOTO-1, JOJO-1, POPO-3, LOLO-1, BOBO-3, YOYO-3, TOTO-3, PO-PRO-1, BO-PRO-1, YO-PRO-1, TO-PRO-1, JO-PRO-1, PO-PRO-3, LO-PRO-1, BO-PRO-3, YO-PRO-3, TO-PRO-3, TO-PRO-5, acridine homodimer, 7-amino actinomycin D, ethidium bromide, ethidium homodimer-1, ethidium homodimer-2, ethidium nonazide, nuclear yellow, propidium iodide. Other useful dyes include those from SYTO 40 blue, green, orange and red fluorescent dyes, Hoechst dyes and dihydroethidium. To enhance the signal, nanoparticles, such as quantum dots and metallic nanoparticles, can be introduced. The particles can be tagged with targeting molecules. Sorting efficiency can be greater than 90%, while sperm viability rates are greater than 30%, typically greater than 90%. Alternatively, instead of electroporating the cells, the dye is introduced into the cells by osmotic gradients. Cells are first incubated in hypertonic conditions, and then transferred to hypotonic conditions; the DNA-staining dye can be added to either, or both, hypertonic and hypotonic solutions. After dying the cells, they are ready to be sorted or further processed.

In a third aspect, the invention provides methods to pre-select the sex of a mammalian offspring, where the sperm are sorted according to the methods of the invention, and then inseminating a female animal of the same species as the male animal that provided the sperm. In a fourth aspect, instead of inseminating a female animal, an egg from a female animal is fertilized in vitro.

DETAILED DESCRIPTION

Figure 1A:
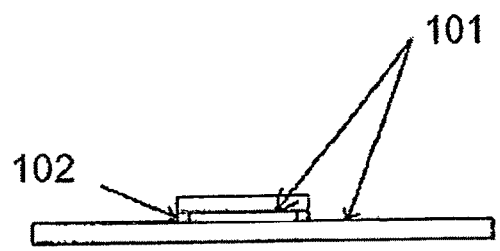
FIG. 1A shows a schematic of an electroporation cell

While the present invention is susceptible of embodiment in many different forms, there are shown in the drawings and described herein in detail specific embodiments thereof, with the understanding that the present disclosure is to be considered as an exemplification of the principles of the invention and is not intended to limit the invention to the specific embodiments illustrated.

The present invention solves the problem of breaching the cell membrane barrier to introduce cellular stains and nanoparticles without killing the cells. Using the methods of the invention, populations of millions of living cells can be simultaneously stained and are appropriate for further applications that require living healthy cells because once applied, staining is immediate.

In some embodiments of the invention, electroporation or osmotic gradients are used to permeabilize cell membranes. Electroporation passes an alternating or direct current (AC or DC) electric field over the cells. The electric shock blasts holes into the cell membrane. Under controlled conditions, the size of the holes are big enough to allow introduction of the stain and/or nanoparticles, but small enough to prevent excessive cytosol leakage and irreparable cell damage that results in cell death. Alternatively, osmotic pressure gradients are used to partially dehydrate the cells. Cells are incubated in a hypertonic solution and then transferred to a hypotonic solution; in either, or both solutions, the dye is added. As the cells reach osmotic equilibrium with the solution, water flows into the cell, drawing in the dye across the cell membrane.

The methods of the invention also provide the unexpected result of hastening the diffusion of membrane permeant dyes into cells.

In addition to introducing stains and dyes into living cells, the methods of the invention also allow the introduction of nanoparticles that can be used as detectable entities in and of themselves (e.g., quantum dots) or to amplify a signal, whether innate to a target molecule or introduced. For example, metallic nanoparticles create surface-enhanced resonances, amplifying the natural fluorescence, auto-fluorescence, or fluorescently stained molecules by orders of magnitude. Using metallic nanoparticles therefore, act as molecular mirrors, deflecting and augmenting available light signals to which they are in close proximity. The nanoparticles prevent energy loss of the stimulating radiation to other modes, like photons, and ensure that the energy is channeled into emitted light. Because the natural fluorescence intensity of some target molecules, such as DNA, is normally very low, amplification of the available signal reduces reliance on dyes or stains which can interfere with normal functioning of the target molecule. For example, many DNA-specific dyes intercalate between the bases; this intercalation can, in mitotically active cells, introduce mutations into genetic code.

Since the methods of the invention allow for fast live-cell staining, other procedural parameters can be optimized to enhance cell viability. For example, the time during which the cells are mixed with the dye can be reduced or even eliminated, conserving cellular resources. The temperatures at which the cells are manipulated and held can also be reduced, effectuating slower cellular metabolism that again conserves cellular resources.

The methods are especially appropriate for sorting sperm by gender, in which quick staining of the sperm avoids the problems of reduced viability because of prolonged incubation times.

DEFINITIONS

Cell-membrane-rupturing-force means force that is sufficient to disrupt a cell membrane such that a cell-impermeant molecule is able to cross the membrane. In the case of cell membrane-permeant molecules, a disrupted membrane permits faster diffusion of the molecule into the cell.

Comparatively high cell viability rate means a rate wherein at least 5% of the total cell population (e.g., a population of sperm) are alive. The rate can be determined by typical viability tests, including exclusion of membrane impermeant dyes (e.g., trypan blue), or for monitoring for a specific cellular activity, such as sperm locomotion.

DNA-staining dye means a detectable substance that interacts with a polynucleotide such that when examined under appropriate conditions, the polynucleotide is optically detected. While most DNA-staining dyes interact directly with polynucleotides (such as Hoechst stains), DNA-staining dyes also encompass those substances that interact with molecules that interact with polynucleotides, such as those that bind DNA-binding proteins, such as transcription factors and histones. In some instances, DNA-staining dye molecules consist of more than one molecule, such as an antibody tagged with a detectable substance, the antibody specifically binding, for example, a DNA-binding protein.

Electroporation means a phenomenon in which the membrane of a cell, exposed to short, high intensity electric field pulses, is temporarily destabilized in specific regions of the cell. During the destabilization period, the cell membrane is highly permeable to exogenous molecules present in the surrounding media. Electroporation is one method of providing a cell membrane-rupturing force.

Hypertonic condition means a condition in which the concentration of electrolyte is above that found in cells in the same solution. In this situation, osmotic pressure leads to the migration of water from the cells to the surrounding solution in an attempt to equalize the electrolyte concentration inside and outside the cell.

Hypotonic condition means a condition in which the concentration of electrolyte is below that found in cells in the same solution. In this situation, osmotic pressure leads to the migration of water into the cells in an attempt to equalize the electrolyte concentration inside and outside the cell.

Nanometallic particle means a nano-scale structure consisting of one or more metals, such as gold, silver, etc.

Permeating and related terms means to breach a cell membrane. Permeating the cell membrane can be accomplished by electroporation and osmotic stress, just as two examples.

Quantum dot means a nano-scale crystalline structure, usually made from cadmium selenide, and absorbs white light and then re-emits it a couple of nanoseconds later in a specific color. The size of a quantum dot varies within the $10^{-9}$ m range, but a quantum dot, regardless of size, is recognizable in that the addition or subtraction of an electron represents a significant change in the particle.

Targeting molecule means a molecule that has an affinity for another molecule or group of molecules. Examples include antibodies, streptavidin, avidin, biotin, etc.

Making and Using the Invention
Electroporation

When a short, high-voltage pulse surpasses the capacitance of a cell membrane, transient—and reversible—disruption of a cell membrane occurs (Gehl, 2003). This disruption allows for easier diffusion of small molecules into the cell, as well as for electrophoretically driving molecules through the destabilized membrane (Gehl, 2003). Any electroporator (an electroporator) or other cell membrane-rupturing-force device which parameters can be manipulated as necessary by the user can be used in the methods of the invention. Examples include the CUY21EDIT Square Wave Electroporator and SONITRON2000 Sonoporator from Nepa Gene (Ichikawa, Chiba; Japan); the EasyjecT Plus, EasyjecT Optima and EasyjecT-Prima (Flowgen; Nottingham, United Kingdom); Gene Pulser Xcell System™ and MicroPulser Electroporator™ (BioRad Laboratories; Hercules, Calif.). Typically, the resistance values range from 2-10,000 ohms ($\Omega$) depending primarily on the electrical conductivity of the buffer. The capacitance varies from 0.1 milliarads (mF) to 1000 mF.

Figure 1B:
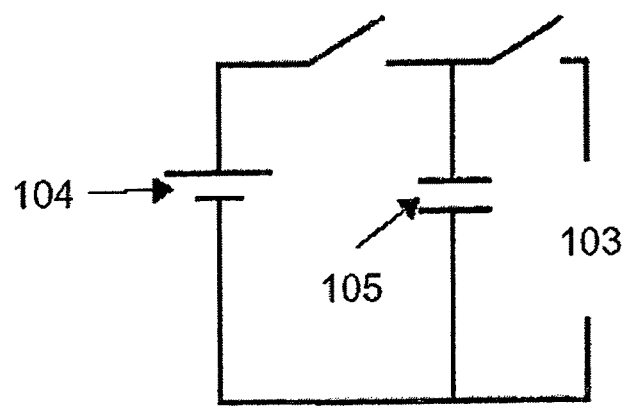
FIG. 1B shows a schematic of a Resistance-Capacitor circuit suitable for electroporation.

One embodiment of a suitable electroporation device is shown in FIG. 1. Referring to FIG. 1A, the electroporation device consists of two parallel glass slides 101 coated with 1,500-2000 angstroms (Å) of indium tin oxide, which are separated by fragments of number 0 glass cover slips 102, yielding a slide separation of 100 millimeters (mm). Referring now to the circuit in FIG. 1B, the sample cell 103 is connected to a resistor-capacitator (RC) circuit by alligator clips. A direct current (DC) power supply 104 is used to charge a capacitor 105. When a switch is thrown, the discharging capacitor generates a time-dependant and spatially uniform electric field across the sample. An oscilloscope is used to monitor the voltage across the sample cell as a function of time. The RC circuit formed by the sample cell and capacitor allow for a well-controlled electric field to be generated. The resistance (R) of the circuit is left floating—that is, determined by the geometry and content of the sample cell.

The temperature at which the cells are subjected to electroporation varies with the cell type and the intended application. For example, in the case of staining mammalian sperm cells for sorting by gender, such as those from bovines, a temperature of about −4° C. to about 39° C.; preferably about 0° C. to about 25° C., more preferably about 0° C. to about 12° C., and most preferably about 0° C., 1° C., 2° C., 3° C., 4° C., 5° C. and 6° C.

Cells are suspended in an osmotically appropriate buffer for electroporation, although the solution can be hyper- or hypotonic to increase the efficiency of electroporation. For example, a 0.35 M sucrose solution yields good results for bovine sperm. Appropriate biological buffers include Hank's Balanced Salt Solution (HBSS), sodium phosphate-based buffers, N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glyclclycine, N-2-hydroxyethylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), and tris (hydroxymethyl)-aminomethane (Tris). Salt solutions that can be used to produce osmotically appropriate conditions include Alseverr's Solution, Dulbecco's Phosphate Buffered Saline (DPBS), Earle's Balanced Salt Solution, Gey's Balanced Salt Solution (GBSS), Puck's Saline A, Tyrode's Salt Solution, St. Thomas Solution and University of Wisconsin Solution. In some instances, a simple sucrose solution is sufficient; in others, a simple buffer.

Because cells differ from organism to organism, of even the same cell type, the parameters for electroporation may need to be determined experimentally. An assay is provided to determine the appropriate parameters for each cell type.

Assay to Determine Parameters for Electroporation Introduction of Dyes and Nanoparticles Cells are harvested according to established procedures, preferably at 4° C. or other metabolic-suspending temperatures, washed, and re-suspended in an osmotically appropriate buffer, preferably without additional divalent cations, such as $Ca^{2+}$, $Mg^{2+}$ and $Mn^{2+}$, at a concentration of $1-2\times 10^7$ cells per ml. The concentration of the cells can be altered to accommodate the differences in cell size and other variables. The desired dye and/or nanoparticles are added to the suspension; the concentrations of which can be experimentally determined. In the case of dyes wherein the binding sites are known (e.g., intercalation between adenosine and threonine in DNA), an estimate of the appropriate dye concentration can be calculated by using an estimate of the amount of DNA in the sample. In some cases, the cells, dye and/or nanoparticles are incubated in the electroporation cell for a short period of time, e.g., 1-15 minutes, preferably 1-5 minutes, preferably less than 5 minutes, more preferably less than 1 minute, and most preferably 30 seconds at a metabolically-suspending temperature (e.g., 0-4° C.). In other instances, there is no pre-incubation and the cells are electroporated immediately. In the case of nanoparticles, incubation times are minimized to prevent any settling or non random dispersion of the particles. Alternatively, the viscosity of the buffer can be altered to maintain the suspension of particles, such as the addition of a protein (e.g., bovine serum albumin) or inert substance.

An electric pulse is applied; a starting voltage of 2.0 kV represents a reasonable starting point, with the current set at a maximum of 0.9 mA. Adjustable current and wattage dials are set at bare minimum. In some cases, the cells, dye and/or nanoparticles are incubated in the electroporation cell for a short period of time after electroporation, e.g., 1-15 minutes, preferably 1-5 minutes, preferably less than 5 minutes, more preferably less than 1 minute, and most preferably 30 seconds at a metabolically-suspending temperature (e.g., 0-4° C.). In other instances, no post-incubation step is necessary. For other cell types, restoring physiological conditions is paramount to preserve cell viability; for these cells, a recovery solution (e.g., culture media) is added immediately. Cells are then transferred for further processing (e.g., washing, collecting, freezing) and observation. In most cases, a recovery media containing divalent cations is preferable, such as provided in appropriate growth media.

Table 1 presents just one example of an experimental design (adapted from (Potter et al., 1984)); this example is not meant to be limiting. One of skill in the art will know how to manipulate these and other appropriate experimental parameters.

TABLE 1

Example of experimental parameters for determining transfer frequency by electroporation

| Cells | Power supply settings (kV/mA) | Electrode | Temperature (° C.) |
|---|---|---|---|
| A | 1.2/300 | Al | 20 |
| A | 1.2/300 | Al | 20 |
| Temperature and voltage effects | | | |
| A | 1.2/300 | Al | 20 |
| A | 1.2/300 | Al | 0 |
| A | 1.2/300 | Al | 20 |
| A | 4.0/0.9 | Al | 20 |
| A | 4.0/capacitor | Al | 20 |
| A | 1.2/100 | SS | 20 |
| A | 1.2/100 | ss | 0 |

TABLE 1-continued

Example of experimental parameters for determining transfer frequency by electroporation

| Cells | Power supply settings (kV/mA) | Electrode | Temperature (° C.) |
|---|---|---|---|
| A | 1.2/300 | SS | 0 |
| A | 2.0/0.9 | ss | 0 |
| A | 4.0/capacitor | ss | 0 |
| Comparison of cell lines and species | | | |
| A | 4.0/0.9 | Al | 0 |
| B | 4.0/0.9 | Al | 0 |
| C | 4.0/0.9 | Al | 0 |
| D | 4.0/0.9 | Al | 0 |

For bovine sperm, when introducing macromolecules such as DNA, a pulse of 0.25 seconds at 25 μF capacitance and 300 V is sufficient in a 1.4 ml electroporation chamber where the electrodes are 4 mm apart (Rieth et al., 2000). For smaller molecules, shorter pulses (e.g., approximately 0.25 ms) at lower voltages (e.g., approximately 10 V) can be used (see Example 1).

Cells

Cells or tissue samples that are appropriate for the methods of the invention are collected from a subject or a culture. The subject can be a vertebrate, more preferably a mammal, such as a bull, monkey, dog, cat, rabbit, pig, goat, sheep, horse, rat, mouse, guinea pig, etc. Any technique to collect the desired cells may be employed, including biopsy, surgery, scrape (inner cheek, skin, etc.), induced ejaculation (for sperm) and blood withdrawal. Any cultured cell type, whether ex vivo cultured cells from a subject, or a cell line, such as Madin-Darby Canine Kidney (MDCK), HeLa, CaCO-2, immunoglobulin-secreting hybridomas, etc. can also be used in the methods of the invention.

Stains, Dyes and Other Visual Labels

To detect a molecule of interest, a label can be used. The label can be coupled to a binding antibody or other interacting polypeptide, or to one or more particles, such as a nanoparticle. Suitable labels include fluorescent moieties, such as fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3 and 5; phycoerythrin; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives; pyrenes; pyridyloxazole derivatives; dapoxyl dyes; Cascade Blue and Yellow dyes; benzofuran isothiocyanates; sodium tetrafluorophenols; 4,4-difluoro-4-bora-3a,4a-dia-za-s-indacene. In some cases enzymatic moieties can be appropriate, such as alkaline phosphatase or horseradish peroxidase; and radioactive moieties, including $^{35}[S]$ and $^{135}[I]$ labels. The choice of the label depends on the application, the desired resolution and the desired observation methods. For fluorescent labels, the fluorophore is excited with the appropriate wavelength, and the sample observed using a microscope, confocal microscope, or fluorescence-activate cell sorting (FACS) machine. In the case of radioactive labeling, the samples are contacted with autoradiography film and developed; alternatively, autoradiography can also be accomplished using ultrastructural approaches.

Dyes and stains that are specific for DNA (or preferentially bind double stranded polynucleotides in contrast to single-stranded polynucleotides) include Hoechst 33342 (2'-[4-ethoxyphenyl]-5-[4-methyl-1-piperazinyl]-2,5'-bi-1H-benzimidazole) and Hoechst 33258 (2'-[4-ethoxyphenyl]-5-[4-methyl-1-piperazinyl]-2,5'-bi-1H-benzimidazole) and others of the Hoechst series; SYTO 40, SYTO 11, 12, 13, 14, 15, 16, 20, 21, 22, 23, 24, 25 (green); SYTO 17, 59 (red), DAPI, YOYO-1, propidium iodide, YO-PRO-3, TO-PRO-3, YOYO-3 and TOTO-3, SYTOX Green, SYTOX, methyl green, acridine homodimer, 7-aminoactinomycin D, 9-amino-6-chloro-2-methoxyactridine. Tables 1, 2 and 3 list many of the available polynucleotides-specific/chromosome specific stains currently available (Tables 2-4 have been adapted from (Haugland, 2002)).

TABLE 2

Cell membrane-impermeant cyanine nucleic acid stains

| Catalogue #[1] | Dye Name | Ex/Em* | Excitation Source[†] |
|---|---|---|---|
| | SYTOX Dyes | | |
| S11348 | SYTOX Blue | 445/470 | Hg-arc lamp, 436 nm line |
| S7020 | SYTOX Green | 504/523 | Ar-ion laser, 488 nm line |
| S11368 | SYTOX Orange | 547/570 | Nd: YAG laser, 532 nm line |
| | Cyanine Dimers | | |
| P3580 | POPO-1 | 434/456 | Hg-arc lamp, 436 nm line He—Cd laser, 442 nm line |
| B3582 | BOBO-1 | 462/481 | Hg-arc lamp, 436 nm line He—Cd laser, 442 nm line |
| Y3601 | YOYO-1 | 491/509 | Ar-ion laser, 488 nm line |
| T3600 | TOTO-1 | 514/533 | Ar-ion laser, 514 nm line |
| J11372 | JOJO-1 | 529/545 | Nd: YAG laser, 532 nm line |
| P3584 | POPO-3 | 534/570 | Nd: YAG laser, 532 nm line |
| L11376 | LOLO-1 | 565/579 | Kr-ion laser, 568 nm line |
| B3586 | BOBO-3 | 570/602 | Hg-arc lamp, 578 nm line |
| Y3606 | YOYO-3 | 612/631 | Orange He—Ne laser, 594 nm line |
| T3604 | TOTO-3 | 642/660 | He—Ne laser, 633 nm line Kr-ion laser, 647 nm line 635 nm diode laser |
| | Cyanine Monomers | | |
| P3581 | PO-PRO-1 | 435/455 | Hg-arc lamp, 436 nm line He—Cd laser, 442 nm line |
| B3583 | BO-PRO-1 | 462/481 | Hg-arc lamp, 436 nm line He—Cd laser, 442 nm line |
| Y3603 | YO-PRO-1 | 491/509 | Ar-ion laser, 488 nm line |
| T3602 | TO-PRO-1 | 515/531 | Ar-ion laser, 514 nm line |
| J11373 | JO-PRO-1 | 530/546 | Nd: YAG laser, 532 nm line |
| P3585 | PO-PRO-3 | 539/567 | Nd: YAG laser, 532 nm line He—Ne laser, 543 nm line |
| L11377 | LO-PRO-1 | 567/580 | Kr-ion laser, 568 nm line |
| B3587 | BO-PRO-3 | 575/599 | Hg-arc lamp, 578 nm line |
| Y3607 | YO-PRO-3 | 612/631 | He—Ne laser, 594 nm line |

TABLE 2-continued

Cell membrane-impermeant cyanine nucleic acid stains

| Catalogue #[1] | Dye Name | Ex/Em* | Excitation Source[†] |
|---|---|---|---|
| T3605 | TO-PRO-3 | 642/661 | He—Ne laser, 633 nm line Kr-ion laser, 647 nm line |
| T7596 | TO-PRO-5 | 747/770 | Laser diodes |

[1]According to (Haugland, 2002), catalogue numbers are specific to Molecular Probes, Inc.
*Wavelengths of excitation (Ex) and emission (Em) maxima, in nm.
[†]Nearest major emission line of some common light sources.

TABLE 3

Cell-permeant cyanine nucleic acid stains

| Catalogue #[1] | Dye Name* | Ex/Em[†] |
|---|---|---|
| | Blue-fluorescent SYTO dyes | |
| S11351 | SYTO 40 blue-fluorescent nucleic acid stain | 419/445 |
| S11352 | SYTO 41 blue-fluorescent nucleic acid stain | 426/455 |
| S11353 | SYTO 42 blue-fluorescent nucleic acid stain | 430/460 |
| S11354 | SYTO 43 blue-fluorescent nucleic acid stain | 437/464 |
| S11355 | SYTO 44 blue-fluorescent nucleic acid stain | 445/472 |
| S11356 | SYTO 45 blue-fluorescent nucleic acid stain | 452/484 |
| | Green-fluorescent SYTO Dyes | |
| S34854 | SYTO 9 green-fluorescent nucleic acid stain | 483/503 |
| S32704 | SYTO 10 green-fluorescent nucleic acid stain | 484/505 |
| S34855 | SYTO BC green-fluorescent nucleic acid stain | 485/500 |
| S7575 | SYTO 13 green-fluorescent nucleic acid stain | 488/509 |
| S7578 | SYTO 16 green-fluorescent nucleic acid stain | 488/518 |
| S7559 | SYTO 24 green-fluorescent nucleic acid stain | 490/515 |
| S7556 | SYTO 21 green-fluorescent nucleic acid stain | 494/517 |
| S32706 | SYTO 27 green-fluorescent nucleic acid stain | 495/537 |
| S32705 | SYTO 26 green-fluorescent nucleic acid stain | 497/534 |
| S7558 | SYTO 23 green-fluorescent nucleic acid stain | 499/520 |
| S7574 | SYTO 12 green-fluorescent nucleic acid stain | 500/522 |
| S7573 | SYTO 11 green-fluorescent nucleic acid stain | 508/527 |
| S7555 | SYTO 20 green-fluorescent nucleic acid stain | 512/530 |
| S7557 | SYTO 22 green-fluorescent nucleic acid stain | 515/535 |
| S7577 | SYTO 15 green-fluorescent nucleic acid stain | 516/546 |
| S7576 | SYTO 14 green-fluorescent nucleic acid stain | 517/549 |
| S7560 | SYTO 25 green-fluorescent nucleic acid stain | 521/556 |
| | Orange-fluorescent SYTO dyes | |
| S32707 | SYTO 86 orange-fluorescent nucleic acid stain | 528/556 |
| S11362 | SYTO 81 orange-fluorescent nucleic acid stain | 530/544 |
| S11361 | SYTO 80 orange-fluorescent nucleic acid stain | 531/545 |
| S11363 | SYTO 82 orange-fluorescent nucleic acid stain | 541/560 |
| S11364 | SYTO 83 orange-fluorescent nucleic acid stain | 543/559 |
| S11365 | SYTO 84 orange-fluorescent nucleic acid stain | 567/582 |
| S11366 | SYTO 85 orange-fluorescent nucleic acid stain | 567/583 |
| | Red-fluorescent SYTO dyes | |
| S11346 | SYTO 64 red-fluorescent nucleic acid stain | 598/620 |
| S11343 | SYTO 61 red-fluorescent nucleic acid stain | 620/647 |
| S7579 | SYTO 17 red-fluorescent nucleic acid stain | 621/634 |
| S11341 | SYTO 59 red-fluorescent nucleic acid stain | 622/645 |
| S11344 | SYTO 62 red-fluorescent nucleic acid stain | 649/680 |
| S11342 | SYTO 60 red-fluorescent nucleic acid stain | 652/678 |
| S11345 | SYTO 63 red-fluorescent nucleic acid stain | 654/675 |

[1]According to (Haugland, 2002), catalogue numbers are specific to Molecular Probes, Inc.
[†]Wavelengths of excitation (Ex) and emission (Em) maxima, in nm.

TABLE 4

Properties of classic nucleic acid stains

| Catalogue #[1] | Dye Name | Ex/Em* | Fluorescence Emission Color | Applications[†] |
|---|---|---|---|---|
| A666 | Acridine homodimer | 431/498 | Green | Impermeant AT-selective High-affinity DNA binding |

TABLE 4-continued

Properties of classic nucleic acid stains

| Catalogue #[1] | Dye Name | Ex/Em* | Fluorescence Emission Color | Applications† |
|---|---|---|---|---|
| A1310 | 7-AAD (7-amino-actinomycin D) | 546/647 | Red | Weakly permeant<br>GC-selective<br>Flow cytometry<br>Chromosome banding |
| A1324 | ACMA | 419/483 | Blue | AT-selective<br>Alternative to quinacrine for chromosome Q banding |
| D1306, D3571, D21490 | DAPI | 358/461 | Blue | Semi-permeant<br>AT-selective<br>Cell-cycle studies<br>Chromosome and nuclei counterstain<br>Chromosome banding |
| D1168, D11347, D23107 | Dihydroethidium | 518/605 | Red§ | Permeant<br>Blue fluorescent until oxidized to ethidium |
| E1305, E3565‡ | Ethidium bromide | 518/605 | Red | Impermeant<br>dsDNA intercalator<br>Dead-cell stain<br>Chromosome counterstain<br>Flow cytometry<br>Argon-ion laser excitable |
| E1169 | Ethidium homodimer-1 (EthD-1) | 528/617 | Red | Impermeant<br>High-affinity DNA labeling<br>Dead-cell stain<br>Argon-ion and green He—Ne laser excitable |
| E3599 | Ethidium homodimer-2 (EthD-2) | 535/624 | Red | Impermeant<br>Very high-affinity DNA labeling<br>Electrophoresis prestain |
| E1374 | Ethidium monoazide | 464/625 (unbound)** | Red | Impermeant<br>Photocrosslinkable |
| H1398, H3569‡, H21491 | Hoechst 33258 (bis-benzimide) | 352/461 | Blue | Permeant<br>AT-selective<br>Minor groove-binding<br>dsDNA-selective binding<br>Chromosome and nuclear counterstain |
| H1399, H3570‡, H21492 | Hoechst 33342 | 350/461 | Blue | Permeant<br>AT-selective<br>Minor groove-binding<br>dsDNA-selective binding<br>Chromosome and nuclear counterstain |
| H21486 | Hoechst 34580 | 392/498 | Blue | Permeant<br>AT-selective<br>Minor groove-binding<br>dsDNA-selective binding<br>Chromosome and nuclear counterstain |
| H22845 | Hydroxystilbamidine | 385/emission varies with nucleic acid | Varies | AT-selective<br>Spectra dependent on secondary structure and sequence<br>RNA/DNA discrimination |
| L7595 | LDS 751 | 543/712 (DNA)<br>590/607 (RNA) | Red/infrared | Permeant<br>High Stokes shift<br>Long-wavelength spectra<br>Flow cytometry |
| N21485 | Nuclear yellow | 355/495 | Yellow | Impermeant<br>Nuclear counterstain |
| P1304MP, P3566‡, P21493 | Propidium iodide (PI) | 530/625 | Red | Impermeant<br>Dead-cell stain<br>Chromosome and nuclear counterstain |

[1]According to (Haugland, 2002), catalogue numbers are specific to Molecular Probes, Inc.
*Excitation (Ex) and emission (Em) maxima in nm.
†Indication of dyes as "permeant" or "impermeant" are for the most common applications; permeability to cell membranes may vary considerably with the cell type, dye concentrations and other staining conditions.
§After oxidation to ethidium.
**Prior to photolysis; after photolysis the spectra of the dye/DNA complexes are similar to those of ethidium bromide-DNA complexes.

In some cases, such as DNA and certain polypeptides, a physical characteristic of that molecule can be used, such as the innate autofluorescence in DNA. In such cases, signal intensity can be modulated by the introduction of nanoparticles (see Modulating fluorescence signals with nanoparticles, below).

Introducing Dye Via Osmolarity/Osmolality Modulation

The modulation of the concentration of solutes can create an environment that is either hypertonic or hypotonic to cells. By suspending the cells in a hypertonic solution, cells become partially dehydrated. After a short period, they are then transferred to a hypotonic solution. Either, or both solutions can include the dye of interest, but should be present to be available to the cells to enter the cells. Preferably, the dye is present in at least the hypotonic solution. As the cells reach osmotic equilibrium with the solution, water flows into the cell, drawing in the dye across the cell membrane.

Osmolality can be varied by either adding appropriate salts or other solutes that are compatible with the cells of interest (e.g., KCl, NaCl, $MgCl_2$, $MnCl_2$, $CaCl_2$, sucrose, glucose, etc.), or by diluting the solution with water or buffer. After collection, cells are transferred to a hypertonic solution for about 0 to about 15 minutes, preferably, about 1 to about 10 minutes, more preferably about 3 to about 7 minutes, and most preferably about 5 minutes. The temperature of the solution is about −4° C. to about 39° C., preferably about 0° C. to about 25° C., more preferably 0° C. to about 12° C., and most preferably, about 4° C. The cells are then transferred to a hypotonic solution or the solution in which the cells are in is diluted with buffer to create hypotonic conditions. The temperature of the added solution is about −4° C. to about 39° C., preferably about 0° C. to about 25° C., more preferably 0° C. to about 12° C., and most preferably, about 4° C.

Osmolality conditions vary somewhat by cell type. However, for bovine sperm, hypertonic conditions are created at approximately greater than 250 mOsm, whereas hypotonic conditions are created at approximately less than 250 mOsm (Liu and Foote, 1998). Preferred hypotonic osmolalities include 100 mOsm to 249 mOsm; most preferably greater than 150 mOsm, but less than 250 mOsm. Hypertonic molalities include 251 mOsm to 1537 mOsm; preferably 500 mOsm to 963 mOsm; and most preferably greater than 250 mOsm but less than 732 mOsm. The dye can be any of those listed in Tables 2-4 or other appropriate dye.

Modulating Fluorescence Signals with Nanoparticles (Quantum Dots and Metallic Nanoparticles)

Organic and biomolecular fluorophores generally exhibit only moderate Stokes shifts between their excitation and emission spectra, have relatively broad emission spectra, and photobleach when monitored over extended periods of time. A promising alternative to conventional fluorophores is quantum dots (QDs) (Doty et al., 2004).

In one embodiment, the core of a QD consists of a semiconductor nanocrystal, such as CdSe, surrounded by a passivation shell, such as ZnS. Upon absorption of a photon, an electron-hole pair is generated, the recombination of which in ~10-20 ns leads to the emission of a less-energetic photon. This energy, and therefore the wavelength, is dependent on the size of the core (smaller→lower wavelength), which can be varied almost at will by controlled-synthesis conditions (Lidke and Arndt-Jovin, 2004). The surface is coated with a polymer that protects the QD from water and allows for chemical coupling to molecules.

The excitation spectra of QDs are a continuum, rising into the ultraviolet, and the emission spectra are narrow and slightly red-shifted to the band-gap absorption. Thus QDs with different emissions can be excited with a single excitation (Smith and Nie, 2004). The large extinction coefficient and the relatively high quantum yield of QDs, as well as their extraordinary photostability, permit the use of a low sample irradiance and prolonged imaging with a detection sensitivity extending down to the single-QD level.

QDs are commercially available (e.g., Quantum Dot Corp.; Hayward, Calif. and Evident Technologies; Troy, N.Y.) with a variety of conjugated or reactive surfaces, e.g., amino, carboxyl, streptavidin, protein A, biotin, and immunoglobulins. QDs are non-toxic to most cells. For example, tissue culture cells loaded with QDs survive for weeks without diminished growth or division, and the QDs persisted the entire time (Doty et al., 2004). In live animal studies, mice lived normal lives with QDs for months without obvious deleterious effects (Lidke and Arndt-Jovin, 2004). QDs can be introduced into sexual reproductive cells without harm. For example, *Xenopus* embryos injected with QDs did not alter the subsequent phenotype; the QDs were viewable throughout development (Smith and Nie, 2004).

QDs can be targeted to specific areas of the cell, such as the nucleus, by coating them with appropriate molecules, such as DNA-binding molecules (oligonucleotides, DNA-binding proteins, such as histones, transcription factors, polymerases and other molecules of the chromatin, DNA-binding dyes, such as those listed in Tables 2-4, or other small molecules, such as other base intercalators). The particles are suspended with the cells prior to electroporation.

Similarly, metallic nano-particles can be used to enhance any fluorescent signal, such as those made of gold and silver. They can likewise be tagged with targeting molecules such that they are in close proximity of the stained DNA.

Detecting Chromosomal Differences with Nanotransistors and Photo-Activatable Fluorophores The ability to incorporate an indicator that has a strongly non-linear response to DNA amount facilitates measuring DNA content. Ideally, this indicator has very little or no fluorescence for the amount of DNA associated with one chromosome, and large amounts of fluorescence for the amount of DNA associated with another chromosome, although in practice approximations to this non-linear response curve are extremely useful. There are several mechanisms that exist for generating such non-linear fluorescence. Photo-activated fluorophores are one such mechanism. Incorporating a photo-activated fluorophore which has a non-linear response to the usual fluorescence emitted by a DNA stain provides a flexible combination of fluorophores whose properties may be tuned to achieve the desired non-linearity (Hogan, 2005). Such photo-activated fluorophores would not necessarily have to be incorporated into the nucleus of the sperm as they may be tuned to respond to fluorescence from the sperm as a whole. By incorporating molecular or nano-transistors into the medium or the sperm, they act as non-linear amplifiers for fluorescence radiated from DNA, either innate autofluorescence or that generated from a stain. Such nano-transistors have countless embodiments because they can be based on biological proteins, or based on quantum dot transistors. There is a significant advantage in that the light that is measured is provided by a strong "pumping" source as opposed to the weak gating source that is usually associated with natural fluorescence of DNA or staining, like Hoescht stains and others listed in Tables 2-4.

Metallic Nanoparticles and Other Modifiers of Fluorophore Free-Space Spectral Properties Nearby conducing metallic particles, colloids or surfaces can modify free-space spectral conditions of fluorophores such that the incident electric field "felt" by the fluorophore is increased (or decreased), and the rate of radiativity decay can also be modulated (Asian et al., 2004). The radiativity decay rate is that at which a fluorophore emits photons. Because the metallic nanoparticles need to be in close proximity to the fluorescent molecule (approximately about 5 nm), particles can be tagged with fluorescent molecules; or, in the case of polynucleotides (which have a low level of auto fluorescence at 260 nm and 280 nm), tagged with molecules that bind the polynucleotides, such as oligonucleotides, small molecules, or polynucleotide specific binding polypeptides. The particles are suspended with the cells prior to electroporation.

Flow Cytometry/Fluorescence-Activated Cell Sorting (FACS)

Methods of performing flow cytometry are well known (Lidke and Arndt-Jovin, 2004). Flow cytometry (measurement of cells as they flow by a detector) has been available for analysis and sorting a variety of cell types in fluid suspension since the late 1970s. Flow cytometers use focused laser light to illuminate cells as they pass the laser beam, one at a time, in a fine fluid stream. Light scattered by the cells and light emitted by fluorescent dyes attached or loaded in the cells are analyzed by detectors. Cells can be distinguished and selected on the basis of size and shape, as well as by the presence of different molecules inside and on the surface of the cells.

Figure 2:
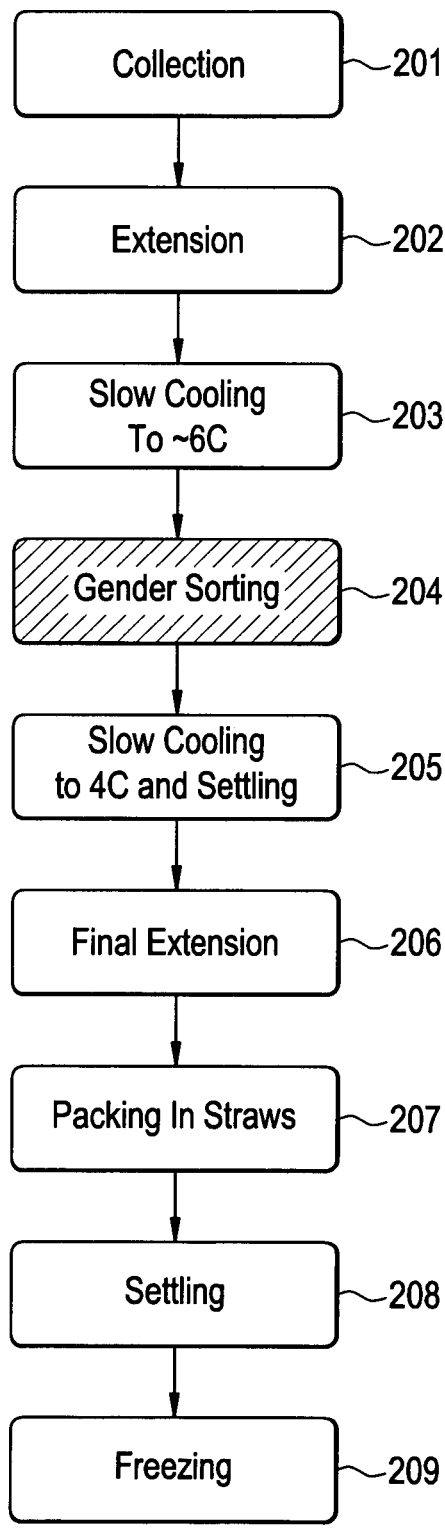
FIG. 2 outlines the steps for collecting, sorting and freezing bovine sperm.

FIG. 2 outlines the flow that can be applied to gender-sorting of sperm. The sperm are collected from the donor 201 and subjected to extension 202 and then cooled slowly to 6° C. Once cooled, the sperm can be subjected to staining DNA by any technique, but preferably the novel techniques of the present invention, using electroporation or osmolality and/or nanoparticles of various compositions. The stained cells are introduced into a cell sorting device 204 and separated based on gender difference, usually by the sex chromosomes X and Y. The sorted cells are collected, and slowly cooled to 4° C. 205 before being subjected to a final extension 206. The cells are loaded into cryogenic-compatible straws 207, the cell allowed to settle 208, and then frozen 209.

In the methods of the invention, because of the advantages of staining cells at 4° C. or even cooler, the cells may be cooled to greater than 6° C. as shown in step 203. Sorting itself 204 can also take place at cooler temperatures, thus preserving cell integrity and cell viability. In many bovine sperm separation protocols, eggs, egg yolks or other sperm-supporting substances are added to the collected sperm to improve viability; however, because the present invention allows for staining and sorting of the cells at cool temperatures—those in which the cells are metabolically inactive, or nearly so ("metabolically suspended")—such a step (and the potential of introducing a confounding variable in sorting, being obliged to pre-filter before sorting, and potentially contaminating the sample with microbes) can be eliminated, or the quantity of added egg or other sperm-supporting substances can be reduced to facilitate sorting and other processing.

Eliminating Dead Cells

After electroporation or osmotic introduction of dyes and/or nanoparticles, a portion of the cell population will usually be nonviable. To increase the quality of the output of the cell populations at the end of processing the cells, dead cells can be removed from the live cells.

In the case of using fluorescent dyes, such as those that bind DNA listed in Tables 2-4, dead cells and successfully stained, viable cells, both fluoresce. This is because dead cells have compromised cell membranes. To eliminate dead cells from the population, one approach is to add a counter-stain that diminishes the signal. For example, in sperm, membrane-impermeant red food coloring is mixed with the cells. By first dyeing the sperm with an impermeable dye, the Hoechst dye is not able to bind to the DNA since the impermeable dye is already bound. Therefore, the fluorescence of the dead sperm should be either eliminated or a different color, depending on the impermeable DNA dye used. Other classic tests include Trypan blue exclusion, where only non-viable cells allow entry of the dye, diminishing fluorescent signals. In this case, the dye is added after electroporation or osmotic shock, but before sorting.

EXAMPLES

The following example is for illustrative purposes only and should not be interpreted as limitations of the claimed invention. There are a variety of alternative techniques and procedures available to those of skill in the art which would similarly permit one to successfully perform the intended invention.

Example 1

In Vivo Staining of Sperm Cells with a DNA-Specific Dye

Methods and Materials

Electroporation Unit

A sample cell was formed by two parallel glass slides coated with 1,500-2000 angstroms (Å) of indium tin oxide (ITO). The slides were separated by fragments of number zero glass cover slips, yielding a slide separation of 100 millimeters (mm).

The sample cell was connected to a resistor-capacitator (RC) circuit by alligator clips. A direct current (DC) power supply was used to charge a capacitor. When a switch was thrown, the discharging capacitor generated a time-dependant and spatially uniform electric field across the sample. An oscilloscope was used to monitor the voltage across the sample cell as a function of time.

The RC circuit formed by the sample cell and capacitor allowed for a well-controlled electric field to be generated. The resistance (R) of the circuit was left floating—that is, determined by the geometry and content of the sample cell. Typical R values ranged from 2-10,000 watts (W) depending primarily on the electrical conductivity of the buffer. The capacitance was varied from 0.1 millifarads (mF) to 1000 mF.

Cells

Bovine sperm that had been previously frozen were thawed for 60 seconds in a 96° F. water bath. Sperm were then centrifuged at 2,000 rotations per minute (rpm) for two minutes and the supernatant decanted. Sperm were then re-suspended with 0.35 M sucrose to partially dehydrate the sperm. The sperm solution was then incubated at 96° F. for 15 minutes and then transferred to the sample cell of the electroporation unit.

Electroporation

A voltage was applied to the capacitor circuit, and then the power supply was disconnected. A switch was then thrown and the capacitor discharged across the sample cell. These steps were carried out within 15 seconds of transferring the sperm to the sample cell to retain a random orientation of sperm with respect to the electric field. Electroporation was carried out on sperm in isotonic (0.25 M sucrose) and hypertonic (0.35 M sucrose) solutions. In each case, 10 V was applied to the capacitor and a time constant of 0.26 milliseconds (ms) measured.

A solution of 0.1 M sucrose and the DNA-specific dye, propidium iodide, was then injected into the sample cell. Fluorescence microscopy is used to image the sperm.

Results

Since propidium iodide dye does not breach the cell membrane barrier, only cells that have had their membranes compromised, such as by electroporation, allow entry of the dye, which then binds to any DNA in the cell (the nucleus and mitochondria), and, when excited with the appropriate wavelength of light, fluoresces. To distinguish fluorescent dead cells from fluorescent live cells, sperm motility was assessed.

In each case (isotonic and hypertonic/hypotonic solution), motile and fluorescent sperm were observed. However, the number of these sperm was enhanced by approximately five-ten fold in the hypertonic/hypotonic solution. Control samples unexposed to electric fields did not yield motile and fluorescent sperm.

Motility was examined in the hypertonic/hypotonic solution and compared to a control sample unexposed to an electric field. The electroporated sample yielded a loss of 70% of motile sperm compared to the control. In addition, the electroporated sample showed a 68% increase in the number of damaged and non-motile sperm. All of the observed motile sperm in the hypertonic/hypotonic solution exposed to the electric field displayed fluorescence.

Larger field strengths, multiple pulses, alternating current (AC) fields, buffers with larger osmotic pressures, and longer time constants led to complete loss of sperm motility. Weaker field strengths and shorter time constants did not yield fluorescent motile sperm.

A temporary spatially uniform electric field allows non-permeant membrane dyes to cross bovine sperm cell membranes. A 70% loss in motility was associated with this process—but manipulating procedure parameters can reduce the death toll. This technique also allows for the introduction of nanoparticles into sperm and other membrane bound-cells.

We claim:

1. A method which distinguishes bovine sperm cells based on DNA content, wherein live sperm cells are stained with a DNA-selective fluorescent dye in an osmotic gradients process, comprising:
   incubating the live sperm cells in a buffer-containing first solution in a hypertonic condition to partially dehydrate the sperm cells, at a temperature between about 0° C. and about 12° C., which is substantially sufficient to maintain a comparatively high sperm viability rate, and for a time period less than about 5 minutes;
   transferring the solution containing the sperm cells to a buffer-containing second solution in a hypotonic condition at said same temperature between about 0° C. and about 12° C.;
   wherein the hypertonic condition is about more than 250 mOsm and the hypotonic condition is about less than 250 mOsm, for bovine sperm cells;
   wherein the dye is present in at least one of the hypertonic or hypotonic condition to expedite permeation of the dye into the sperm cells when osmotic equilibrium is reached, thereby staining DNA in the sperm cells;
   exposing the sperm cells to a light source to cause the stained DNA to fluoresce;
   detecting a pre-determined fluorescence of the stained DNA, the predetermined fluorescence corresponding to DNA content;
   distinguishing the sperm cells based on the pre-determined fluorescence; and
   collecting selected sperm cells.

2. The method of claim 1, wherein an incubation temperature of said sperm cells is less than or equal to about 4° C.

3. The method of claim 1, wherein the high sperm viability rate is greater than 70%.

4. The method of claim 1, wherein said dye is present in the second solution in the hypotonic condition, and said dye is drawn into the sperm cells across the cell membrane.

5. The method of claim 4, wherein said temperature is about 4 degrees Centigrade.

6. The method of claim 4, further comprising:
   reducing one of a time or a temperature during which the sperm cells are mixed with the dye, to conserve cellular resources.

7. The method of claim 1, wherein said fluorescence is photoactivated.

8. The method of claim 1, further comprising:
   collecting the sperm cells from a donor and subjecting the sperm cells to extension, prior to incubation; and
   cooling the sperm cells to 6 degrees Centigrade.

9. The method of claim 8, further comprising:
   cooling the collected sperm cells after the collecting step, to about 4 degrees Centigrade;
   subjecting the collected sperm cells to a second extension; and
   freezing the collected sperm cells.

10. The method of claim 9, further comprising:
    adding a sperm-supporting substance, including eggs or egg yolks, to said collected bovine sperm cells, to extend sperm viability.

11. The method of claim 1, wherein the selected sperm cells are sorted into X and Y chromosomes for gender sorting.

12. The method of claim 1, further comprising:
    adding a counter-stain to the sperm cells which one of diminishes fluorescence or stains in another color, to identify dead sperm cells from live sperm cells; and
    removing said dead sperm from said live sperm.

13. The method of claim 1, wherein the dye comprises at least one selected from the group consisting of SYTOX blue, SYTOX green, SYTOX orange, a cyanine dimer, POPO-1, BOBO-1, YOYO-1, TOTO-1, JOJO-1, POPO-3, LOLO-1, BOBO-3, YOYO-3, TOTO-3, a cyanine monomer, PO-PRO-1, BO-PRO-1, YO-PRO-1, TO-PRO-1, JO-PRO-1, POPRO-3, LO-PRO-1, BO-PRO-3, YO-PRO-3, TO-PRO-3, TO-PRO-5, acridine homodimer, 7-amino actinomycin D, ethidium bromide, ethidium homodimer-1, ethidium homodimer-2, ethidium nonazide, nuclear yellow, and propidium iodide.

14. The method of claim 1, wherein the dye comprises at least one selected from the group consisting of SYTO 40 blue-fluorescent nucleic acid stain, SYTO 41 blue, SYTO 42 blue, SYTO 43 blue, SYTO 44 blue, SYTO 45 blue, a green-fluorescent SYTO dye, SYTO 9 green, SYTO 10 green, SYTO BC green, SYTO 1 green, SYTO 16 green, SYTO 24 green, SYTO 21 green, SYTO 27 green, SYTO 26 green, SYTO 23 green, SYTO 12 green, SYTO 11 green, SYTO 20 green, SYTO 22 green, SYTO 15 green, SYTO 14 green, SYTO 25 green, an orange-fluorescent SYTO dye, SYTO 86 orange, SYTO 81 orange, SYTO 80 orange, SYTO 82 orange, SYTO 83 orange, SYTO 84 orange, SYTO 85 orange, a red-fluorescent SYTO dye, SYTO 64 red, SYTO 61 red, SYTO 17 red, SYTO 59 red, SYTO 62 red, SYTO 60 red, SYTO 63 red, a Hoechst dye, Hoechst 33342, Hoechst 34580, Hoechst 33258, DAPI, LDS 751 and dihydroethidium.

15. The method of claim 1, further comprising:
   introducing nanoparticles into the sperm cells to be one of detected, or to amplify the fluorescence of the DNA.

16. The method of claim 15, wherein said nanoparticles are quantum dots or nano-metallic particles.

17. The method of claim 1, wherein osmolality is varied by adding salts or solutes compatible with the sperm cells, or by dilution of the second solution in the hypotonic condition, with water or buffer.

18. The method of claim 1, wherein in the transferring step, the hypotonic condition is created by addition of buffer.

19. A method which distinguishes bovine sperm cells based on DNA content, wherein live sperm cells are stained with a DNA-selective fluorescent dye in an osmotic gradients process, comprising:
   incubating the live sperm cells in a buffer-containing first solution in a hypertonic condition to partially dehydrate the sperm cells, at a temperature between about 0° C. and about 12° C., which is substantially sufficient to maintain a comparatively high sperm viability rate, and for a time period less than about 5 minutes;
   transferring the solution containing the sperm cells to a buffer-containing second solution in a hypotonic condition at said same temperature between about 0° C. and about 12° C.;
   wherein the hypertonic condition is about more than 500 mOsm and the hypotonic condition is about less than 250 mOsm, for bovine sperm cells;
   wherein the dye is present in at least one of the hypertonic or hypotonic condition to expedite permeation of the dye into the sperm cells when osmotic equilibrium is reached, thereby staining DNA in the sperm cells;
   exposing the sperm cells to a light source to cause the stained DNA to fluoresce;
   detecting a pre-determined fluorescence of the stained DNA, the predetermined fluorescence corresponding to DNA content;
   distinguishing the sperm cells based on the pre-determined fluorescence; and
   collecting selected sperm cells.

20. A method which distinguishes bovine sperm cells based on DNA content, wherein live sperm cells are stained with a DNA-selective fluorescent dye in an osmotic gradients process, comprising:
   incubating the live sperm cells in a buffer-containing first solution in a hypertonic condition to partially dehydrate the sperm cells, at a temperature between about 0° C. and about 12° C., which is substantially sufficient to maintain a comparatively high sperm viability rate, and for a time period less than about 5 minutes;
   transferring the solution containing the sperm cells to a buffer-containing second solution in a hypotonic condition at said same temperature between about 0° C. and about 12° C.;
   wherein the hypertonic condition is about more than 250 mOsm and the hypotonic condition is greater than 150 mOsm, but less than 250 mOsm, for bovine sperm cells;
   wherein the dye is present in at least one of the hypertonic or hypotonic condition to expedite permeation of the dye into the sperm cells when osmotic equilibrium is reached, thereby staining DNA in the sperm cells;
   exposing the sperm cells to a light source to cause the stained DNA to fluoresce;
   detecting a pre-determined fluorescence of the stained DNA, the predetermined fluorescence corresponding to DNA content;
   distinguishing the sperm cells based on the pre-determined fluorescence; and
   collecting selected sperm cells.

* * * * *